(12) United States Patent
Shimada

(10) Patent No.: US 9,265,670 B2
(45) Date of Patent: Feb. 23, 2016

(54) METHOD AND DEVICE FOR PRODUCING DISPOSABLE WORN ARTICLE

(71) Applicant: Takahiro Shimada, Osaka (JP)

(72) Inventor: Takahiro Shimada, Osaka (JP)

(73) Assignee: ZUIKO CORPORATION, Osaka (JP)

( * ) Notice: Subject to any disclaimer, the term of this patent is extended or adjusted under 35 U.S.C. 154(b) by 85 days.

(21) Appl. No.: 14/374,425

(22) PCT Filed: Apr. 16, 2013

(86) PCT No.: PCT/JP2013/061252
§ 371 (c)(1),
(2) Date: Jul. 24, 2014

(87) PCT Pub. No.: WO2013/157533
PCT Pub. Date: Oct. 24, 2013

(65) Prior Publication Data
US 2015/0024919 A1 Jan. 22, 2015

(30) Foreign Application Priority Data

Apr. 19, 2012 (JP) ................................. 2012-095596
Apr. 19, 2012 (JP) ................................. 2012-095597

(51) Int. Cl.
*A61F 13/44* (2006.01)
*A61F 13/49* (2006.01)
(Continued)

(52) U.S. Cl.
CPC ..... *A61F 13/49058* (2013.01); *A61F 13/15756* (2013.01); *A61F 13/49* (2013.01);
(Continued)

(58) Field of Classification Search
CPC ................... A61F 13/49058; A61F 13/15756; A61F 13/5622; A61F 13/49; B65H 35/08; B65H 2301/4472; B65H 2301/44512; B65H 2406/345; B65H 2301/44552; B65G 47/32; B65G 47/84

USPC ................................................... 83/42, 50, 37
See application file for complete search history.

(56) References Cited

U.S. PATENT DOCUMENTS 4,171,239 A * 10/1979 Hirsch .............. A61F 13/15756
156/461
4,617,082 A * 10/1986 Oshefsky .......... A61F 13/15609
156/164

(Continued)

FOREIGN PATENT DOCUMENTS

| JP | 2006-212307 A | 8/2006 |
| JP | 2010-530269 A | 9/2010 |
| JP | 2011-025079 A | 2/2011 |

OTHER PUBLICATIONS

International Search report for corresponding International Application No. PCT/JP2013/061252 mailed Jul. 9, 2013.

*Primary Examiner* — Sean Michalski
(74) *Attorney, Agent, or Firm* — Renner, Otto, Boisselle & Sklar, LLP

(57) ABSTRACT

A method includes: a severing step of successively producing a plurality of panels from a continuous web; an interval-increasing step of increasing an interval in width direction between a pair of panels, adjacent to each other in flow direction; a receiving step of receiving the panels by first and second rollers at first and second receiving positions, which are separated from each other in flow direction, wherein the first and second rollers for receiving the panels are placed so that axial lines of the first and second rollers are placed offset from each other in flow direction of the panels; and a placement step for placing the panels, from the rollers at first and second hand-over positions which are separated from each other in flow direction, onto opposite side portions of a body portion at the same position in the longitudinal direction of the body portion.

16 Claims, 9 Drawing Sheets

(51) Int. Cl.
*A61F 13/56* (2006.01)
*A61F 13/15* (2006.01)
*B65G 47/32* (2006.01)
*B65G 47/84* (2006.01)
*B65H 35/08* (2006.01)

(52) U.S. Cl.
CPC ............ *A61F13/5622* (2013.01); *B65G 47/32* (2013.01); *B65G 47/84* (2013.01); *B65H 35/08* (2013.01); *B65H 2301/4472* (2013.01); *B65H 2301/44512* (2013.01); *B65H 2301/44552* (2013.01); *B65H 2406/345* (2013.01)

(56) References Cited

U.S. PATENT DOCUMENTS

| | | | | |
|---|---|---|---|---|
| 4,701,239 A * | 10/1987 | Craig | A61F 13/15756 | 156/519 |
| 5,049,219 A * | 9/1991 | Johns | B29C 66/7392 | 156/250 |
| 5,399,219 A * | 3/1995 | Roessler | A61F 13/15756 | 156/229 |
| 5,640,752 A * | 6/1997 | Steiner | H01F 41/0233 | 29/564.1 |
| 5,702,551 A * | 12/1997 | Huber | A61F 13/15756 | 156/164 |
| 6,009,781 A * | 1/2000 | McNeil | B26D 1/405 | 83/304 |
| 6,730,189 B1 * | 5/2004 | Franzmann | A61F 13/15756 | 156/265 |
| 6,736,923 B1 * | 5/2004 | Franzmann | A61F 13/15626 | 156/265 |
| 6,783,487 B2 * | 8/2004 | Duhm | A61F 13/15804 | 156/66 |
| 6,925,693 B2 * | 8/2005 | Takeuchi | H01L 41/0946 | 264/434 |
| 7,192,502 B2 * | 3/2007 | Spatafora | B65C 1/023 | 156/249 |
| 7,258,049 B2 * | 8/2007 | Grafe | B23D 25/12 | 225/2 |
| 7,341,087 B2 * | 3/2008 | Tabor | A61F 13/15764 | 156/538 |
| 7,713,371 B2 * | 5/2010 | Lohrengel | A61F 13/15756 | 156/250 |
| 7,811,403 B2 * | 10/2010 | Andrews | A61F 13/15756 | 156/238 |
| 7,871,400 B2 * | 1/2011 | Sablone | A61F 13/15699 | 604/385.01 |
| 7,931,638 B2 * | 4/2011 | Yao | A61F 13/15699 | 604/367 |
| 8,172,977 B2 * | 5/2012 | McCabe | A61F 13/15756 | 156/250 |
| 8,216,414 B2 * | 7/2012 | Hornung | A61F 13/15203 | 156/164 |
| 8,221,372 B2 * | 7/2012 | Kouno | A61F 13/5148 | 604/385.04 |
| 8,622,983 B2 * | 1/2014 | Wilkes | A61F 13/15609 | 156/226 |
| 8,833,750 B2 * | 9/2014 | Knauer | B41F 13/56 | 270/10 |
| 8,945,080 B2 * | 2/2015 | Nishida | A61F 13/62 | 604/387 |
| 9,003,937 B2 * | 4/2015 | Nobukuni | B26D 1/605 | 83/298 |
| 2003/0047273 A1 * | 3/2003 | Kojo | A61F 13/15609 | 156/250 |
| 2007/0142808 A1 | 6/2007 | Wada et al. | | |
| 2010/0192739 A1 | 8/2010 | Piantoni et al. | | |
| 2015/0166294 A1 * | 6/2015 | Perego | B65H 35/08 | 83/155 |

\* cited by examiner

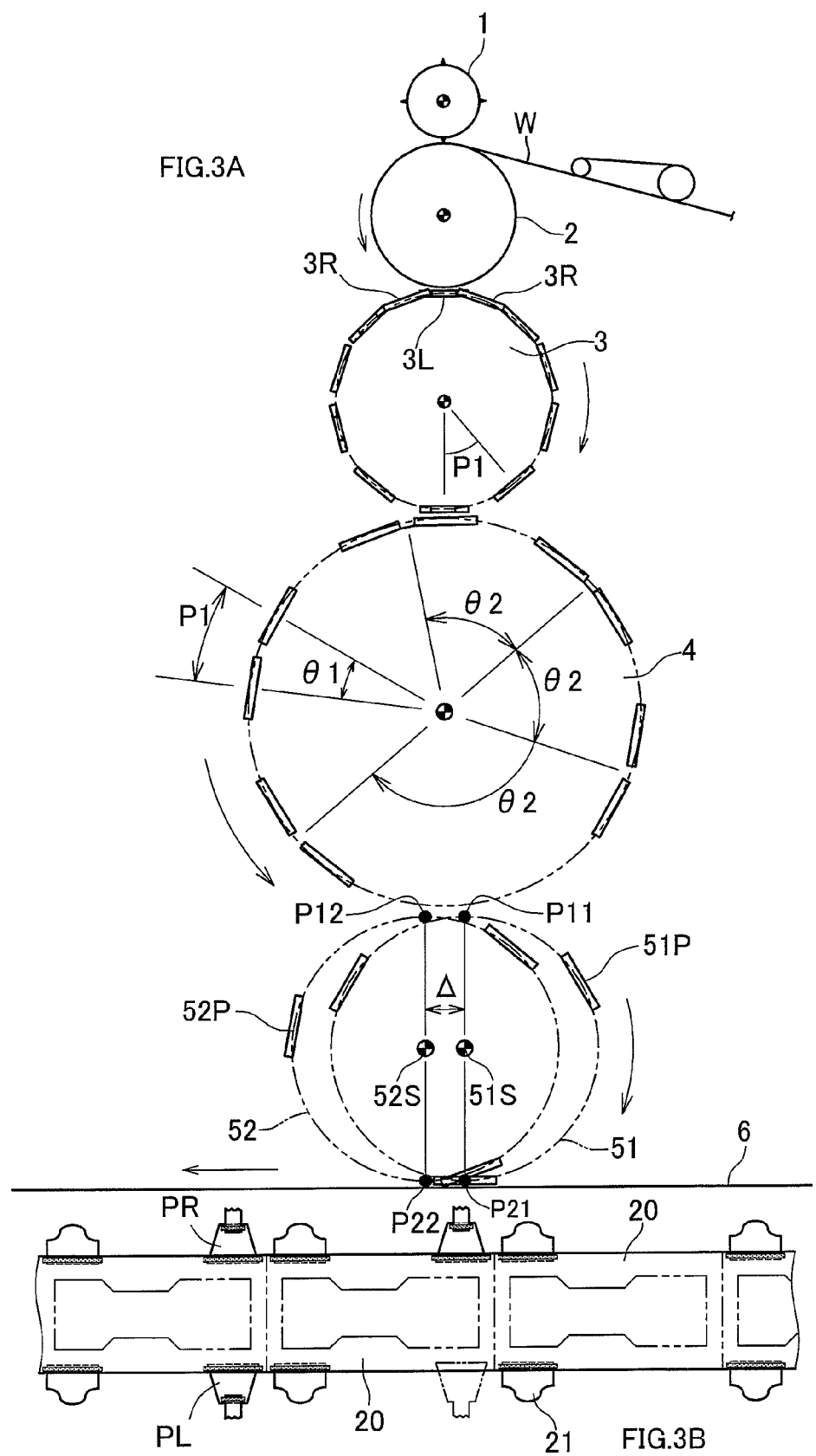

METHOD AND DEVICE FOR PRODUCING DISPOSABLE WORN ARTICLE

TECHNICAL FIELD

The present invention relates to a method and a device for producing a disposable worn article.

BACKGROUND ART

As a method for producing a worn article of this type, a method has been known in which a pair of panels are fastened to the left and the right sides of a body portion of a diaper in the girth direction (the first patent document).

CITATION LIST

Patent Literature

[First Patent Document] JP2010-530269A (FIGS. 1 to 6)

SUMMARY OF INVENTION

However, with the invention of the first patent document, the carrying speed of a pair of panels is controlled together with the rotation speed of the alignment roller so that the pair of panels are at the same position in the longitudinal direction of the body portion of the diaper. With such a speed control, typically, the mechanism for the speed control inevitably becomes complicated.

It is therefore an object of the present invention to provide a method and a device for producing a disposable worn article, with which the mechanism for placing panels at the same position in the longitudinal direction of the body portion will unlikely be complicated.

A production method of the present invention in one aspect is a method for producing a disposable worn article, in which a pair of panels are fastened to a body portion at the same position in a longitudinal direction thereof and in left and right opposite side portions in a girth direction thereof, the method including:

a severing step of successively severing tip portions of a continuous web in a flow direction, the continuous web being continuous in the flow direction, along a virtual severing line extending in a width direction perpendicular to the flow direction, thereby successively producing a plurality of panels;

an interval-increasing step of increasing an interval in the width direction between a pair of panels, adjacent to each other in the flow direction, of the plurality of panels;

a receiving step of receiving the panels by first and second rollers at first and second receiving positions, which are separated from each other in the flow direction, wherein the first and second rollers are placed so that a first axial line of the first roller for receiving and holding one of the pair of panels separated from each other in the width direction and a second axial line of the second roller for receiving and holding the other one of the pair of panels are placed offset from each other in the flow direction of the panels; and a placement step of placing the panels, from the first and second rollers at first and second hand-over positions which are separated from each other in the flow direction, onto the opposite side portions of the body portion at the same position in the longitudinal direction of the body portion.

Note that "extending in a width direction perpendicular to the flow direction" means to also include a case of extending both in the width direction and in the flow direction, as well as a case of extending only in the width direction.

On the other hand, a production device of the present invention in one aspect is a device for producing a disposable worn article, in which a pair of panels are fastened to a body portion at the same position in a longitudinal direction thereof and in left and right opposite side portions in a girth direction thereof, the device including:

a cutter for successively severing tip portions of a continuous web in a flow direction, the continuous web being continuous in the flow direction, along a virtual severing line extending in a width direction perpendicular to the flow direction, thereby successively producing a plurality of panels;

an interval-increasing drum for increasing an interval in the width direction between a pair of panels, adjacent to each other in the flow direction, of the plurality of panels; and a phase wheel for receiving the panels by first and second rollers at first and second receiving positions, which are separated from each other in the flow direction, wherein the first and second rollers are placed so that a first axial line of the first roller for receiving and holding one of the pair of panels separated from each other in the width direction and a second axial line of the second roller for receiving and holding the other one of the pair of panels are placed offset from each other in the flow direction of the panels, and for placing the panels, from the first and second rollers at first and second hand-over positions which are separated from each other in the flow direction, onto the opposite side portions of the body portion at the same position in the longitudinal direction of the body portion.

In these cases, the first axial line of the first roller and the second axial line of the second roller are offset from each other by a predetermined offset amount Δ. Therefore, the first roller, of the rollers, offset on the downstream side will receive panels from the interval-increasing drum at a position delayed (downstream) by an amount approximately equal to the offset amount Δ with respect to the second roller.

Moreover, while the rollers place panels on the body portion after rotating about 180°, the first roller offset on the downstream side places panels on the body portion upstream in the flow direction of the body portion by the offset amount Δ, whereas the second roller places panels on the body portion downstream in the flow direction of the body portion by the offset amount Δ. Therefore, again, a panel placed by the first roller will be delayed by an amount approximately equal to the offset amount Δ with respect to the second roller.

Therefore, if the interval P1 between panels to be placed left and right on a single body portion is approximately equal to twice the offset amount Δ, i.e., P1≈2*Δ, they can be placed at the same position in the longitudinal direction of the body portion without performing a complicated speed control.

Incidentally, with the prior art, a pair of trapezoidal panels are transferred on a drum in the width direction of the drum. Therefore, trapezoidal panels may interfere with each other, resulting in a shift in the panel-holding position or creases in the panel.

It is therefore another object of the present invention to provide a method and a device for producing a disposable worn article, which unlikely has a shift in the panel-holding position or creases in the panel.

A production method of the present invention in another aspect is a method for producing a disposable worn article, in which a pair of panels are fastened to a body portion in left and right opposite side portions in a girth direction thereof, the method including:

a severing step of successively severing tip portions of a continuous web in a flow direction, the continuous web being continuous in the flow direction, along a virtual severing line extending in a width direction perpendicular to the flow direction, thereby successively producing a plurality of panels;

a first re-pitching step of increasing an interval in the flow direction between the plurality of panels;

an interval-increasing step of, after the first re-pitching step, increasing an interval in the width direction between a pair of panels, adjacent to each other, of the plurality of panels; and a placement step of, after the interval-increasing step, placing the pair of panels in the opposite side portions of the body portion.

On the other hand, a production device of the present invention in another aspect is a device for producing a disposable worn article, in which a pair of panels are fastened to a body portion in left and right opposite side portions in a girth direction thereof, the device including:

a cutter for successively severing tip portions of a continuous web in a flow direction, the continuous web being continuous in the flow direction, along a virtual severing line extending in a width direction perpendicular to the flow direction, thereby successively producing a plurality of panels;

a first re-pitching drum for increasing an interval in the flow direction between the plurality of panels;

an interval-increasing drum, placed downstream of the first re-pitching drum, for increasing an interval in the width direction between a pair of panels, adjacent to each other, of the plurality of panels; and a phase wheel, placed downstream of the interval-increasing drum, for placing the pair of panels in the opposite side portions of the body portion.

In these cases, before moving panels, obtained by severing a continuous web, in the width direction, the interval between panels adjacent to each other is increased in the first re-pitching step by moving the panels in the flow direction. Therefore, when increasing the interval between panels in the width direction by moving the panels in the width direction, the panels will not interfere with each other. Therefore, there will unlikely be a shift in the panel-holding position or creases due to interference between panels.

Note that "extending in a width direction" means that the virtual severing line may be set to extend in exactly the horizontal direction perpendicular to the flow direction, may be set to extend in a slant direction inclined with respect to the width direction, or may be a quadratic curve, a cubic curve, or the like, instead of a straight line.

For example, even if the virtual severing line is set to extend in exactly the horizontal direction, the panels will not interfere with each other due to a wind pressure, or the like, during the interval-increasing step since the interval between the panels in the flow direction has been increased in advance in the first re-pitching step.

BRIEF DESCRIPTION OF DRAWINGS

FIG. 3A is a schematic side view showing a production device of the present invention, and FIG. 3B is a plan view showing panels being placed on a body portion.

DESCRIPTION OF EMBODIMENTS

Figure 1:
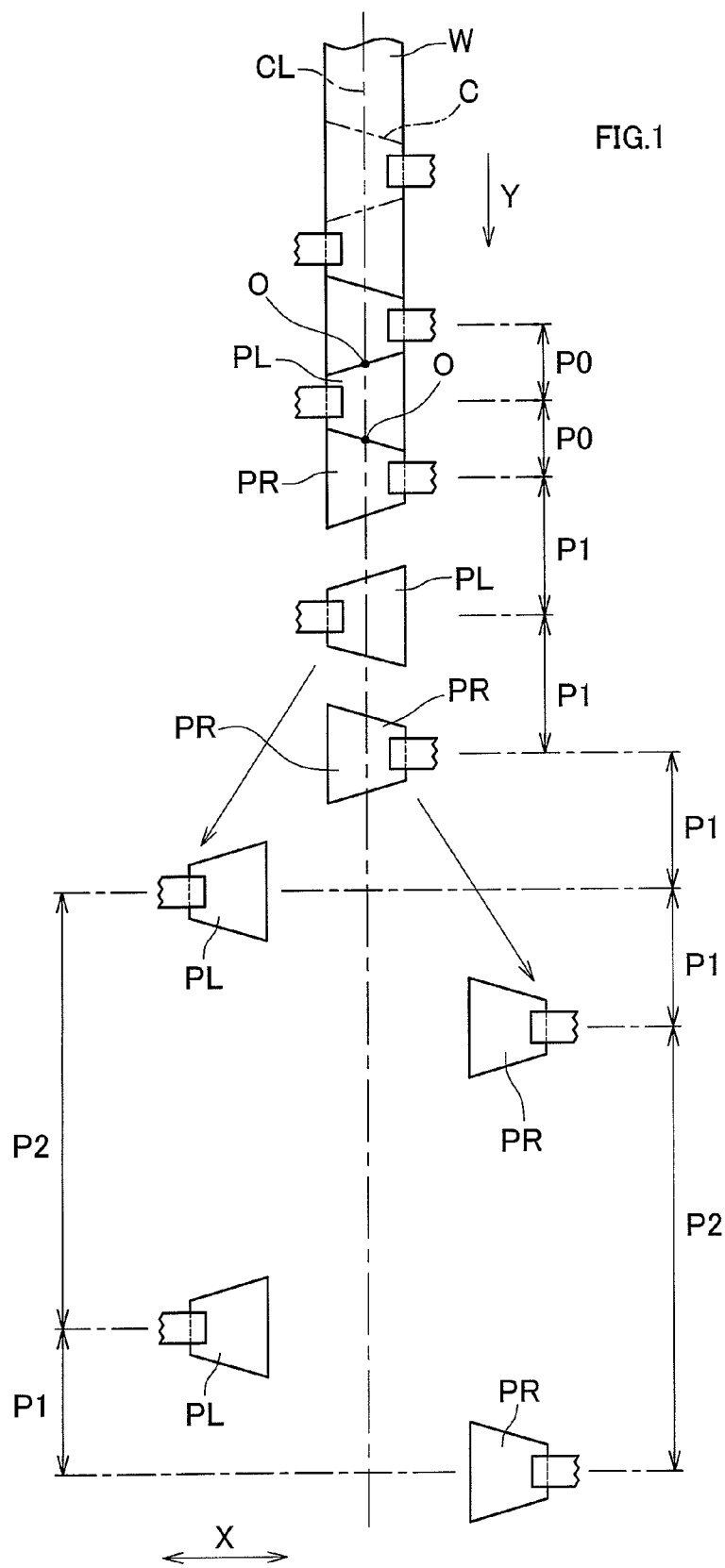
FIG. 1 is a conceptual diagram showing a part of a step of Embodiment 1 of a method for producing a worn article of the present invention.

Preferably, the production method of one aspect further includes a re-pitching step of increasing an interval in the flow direction between a pair of panels, adjacent to each other in the flow direction, of the plurality of panels.

In this case, it is possible to continuously place panels on body portions adjacent to each other.

Preferably, the method further includes a speed varying step of periodically varying a rotation speed of a plurality of pads of the rollers holding the panels between the receiving step and the placement step a number of times equal to the number of pads for one rotation according to a size of the worn article.

In this case, with electric control using a servo motor, it is possible to use a single production device to produce worn articles of different sizes.

Preferably, in the production device of one aspect, the first and second rollers respectively include a plurality of first and second pads for holding the panels, with the first pads and the second pads being separated from each other in the width direction, and the first axial line being the center of rotation of the first pads and the second axial line being the center of rotation of the second pads are separated from each other in the flow direction.

More preferably, radii of rotation of the first pads and the second pads are equal to each other.

While it is very convenient if the radii of rotation are equal to each other, as described above, the radii of rotation of the first and second rollers do not need to be equal to each other.

More preferably, it further includes a re-pitching drum placed between the cutter and the interval-increasing drum for increasing an interval in the flow direction between a pair of panels, adjacent to each other in the flow direction, of the plurality of panels.

By increasing the interval between a pair of panels by the re-pitching drum, it is possible to continuously place panels on a plurality of body portions.

Preferably, it further includes a variable-speed control device (speed changing controller) for periodically varying a rotation speed of a plurality of pads of the rollers holding the panels, from the receiving until the placement, a number of times equal to the number of pads for one rotation according to a size of the worn article.

In this case, with electric control using a servo motor, it is possible to use a single production device to produce worn articles of different sizes.

Preferably, in the production method of another aspect, the virtual severing line is non-parallel to the width direction, and the tip portions of the continuous web are successively severed in the severing step along the non-parallel severing line, thereby producing the panels.

The term "non-parallel" is a concept excluding a case where the virtual severing line is set to extend in exactly the horizontal direction perpendicular to the flow direction. That is, the virtual severing line may be set to extend in a slant direction inclined with respect to the width direction, or may be a quadratic curve, a cubic curve, or the like, instead of a straight line.

In this case, performing the first re-pitching step prevents panels adjacent to each other in the flow direction from interfering with each other when increasing the interval between the panels in the width direction.

More preferably, it further includes a second re-pitching step of increasing a pair interval between a pair of panels, which have been separated from each other in the flow direction in the first re-pitching step, and another pair of panels adjacent to the pair of panels.

With the second re-pitching step, the pair interval between a pair of panels and an adjacent pair of panels can be made to coincide with, or can be brought closer to, the interval between adjacent body portions. That is, in the placement step, it is possible to place a pair of panels on each body portion while making it coincide with (or bringing it closer to) the interval between adjacent body portions carried in the flow direction.

More preferably, it further includes: a receiving step of successively receiving a plurality of pairs of panels, the pair interval therebetween having been increased after the second re-pitching step, from an upstream device to a downstream device; and a third re-pitching step for further increasing the pair interval after the receiving step.

By performing the third re-pitching step by another device different from that for the second re-pitching step, it is possible to prevent the diameter of the drum responsible for the second re-pitching step from becoming excessive.

Preferably, in the production device of another aspect, the virtual severing line is non-parallel to the width direction, and the tip portions of the continuous web are successively severed by the cutter along the non-parallel severing line, thereby producing the panels.

In this case, increasing the interval in the flow direction between the plurality of panels by the first re-pitching drum prevents panels along the non-parallel severing line from interfering with each other when increasing the interval between the panels in the width direction by the interval-increasing drum.

More preferably, it further includes a second re-pitching drum, placed downstream of the first re-pitching drum, for increasing a pair interval (an interval) between a pair of panels, which have been separated from each other in the flow direction, and another pair of panels adjacent to the pair of panels.

In this case, by the second re-pitching drum, it is possible to increase the pair interval between a pair of panels and another adjacent pair of panels.

More preferably, the phase wheel, placed downstream of the second re-pitching drum, successively receives a plurality of pairs of panels, the pair interval therebetween having been increased, and further increases the pair interval after the receiving.

By further increasing the pair interval by the phase wheel, it is possible to prevent the diameter of the second re-pitching drum from becoming excessive.

Embodiments

The present invention will be understood more clearly from the following description of preferred embodiments taken in conjunction with the accompanying drawings. Note however that the embodiments and the drawings are merely illustrative and should not be taken to define the scope of the present invention. The scope of the present invention shall be defined only by the appended claims. In the accompanying drawings, like reference numerals denote like components throughout the plurality of figures.

Embodiments of the present invention will now be described with reference to the drawings.

First, before describing the present production method and device, an example of a worn article that can be produced by the present production method will be described.

Figure 2:
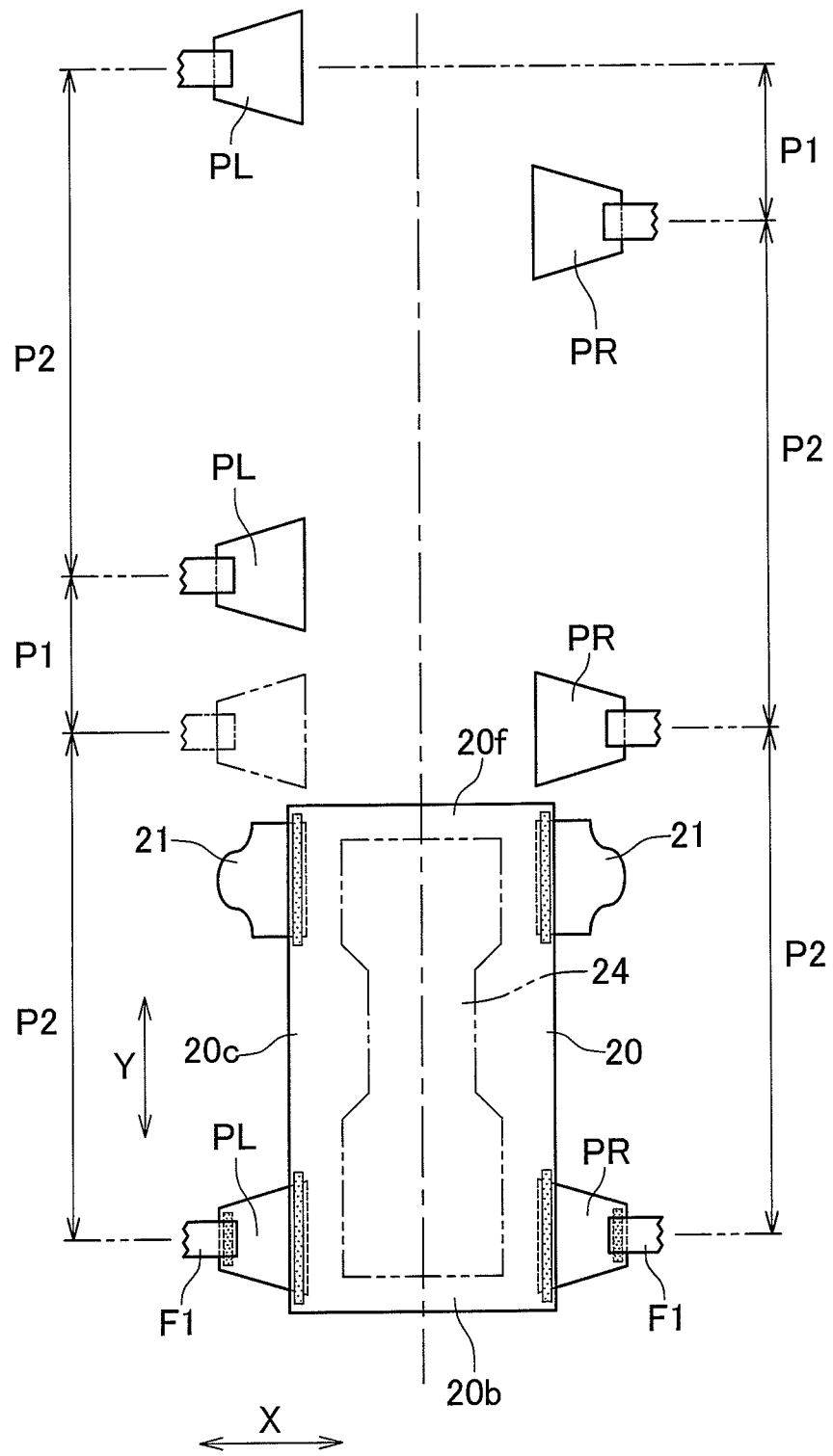
FIG. 2 is a conceptual diagram showing the rest of the same step.

As shown in FIG. 2, the present diaper includes an absorbent body portion 20, a pair of side panels PL and PR fastened to the body portion 20, and a pair of tab members 21 and 21.

The body portion 20 covers the front around-torso area, the crotch area and the rear around-torso area of the wearer when worn. The body portion 20 includes a front torso portion 20$f$, a crotch portion 20$c$ and a rear torso portion 20$b$ corresponding to the respective areas.

The panels PL and PR are each positioned between the front and rear torso portions 20$f$ and 20$b$ when worn. The panels PL and PR are fastened to the left side and the right side, respectively, of an end portion of the body portion 20 in the longitudinal direction Y. For example, the panels PL and PR are fastened to the rear torso portion 20$b$ while projecting from the left and the right of the rear torso portion 20$b$ of the body portion 20. Note that the panels PL and PR may be fastened to the front torso portion 20$f$.

On the other hand, the tab members 21 are fastened to the left and the right of the front torso portion 20$f$ of the body portion 20. Note that the tab members 21 may be omitted.

The panels PL and PR may be formed by, for example, sandwiching an elastic thread (an example of an elastic member) between two sheets of non-woven fabric. Under no load, the panels PL and PR may be in a shrunk state, where the elastic threads are shrunk in the girth direction X to form gathers, as shown in FIG. 2.

Note that a method disclosed in JP63-243309A may be used as the method for placing elastic threads on the panels PL and PR.

The panels PL and PR may be formed by a stretchable non-woven fabric having a stretchability and having no elastic threads.

First touch fasteners (an example of a fastening element) F1 may be fastened to the inner side (the side to be in contact with the skin of a wearer when worn) of the panels PL and PR. On the other hand, second touch fasteners (not shown), which can be fastened to the first touch fastener F1, may be fastened to the outer side (the side to be exposed to the outside when worn) of the front torso portion 20$f$ of the body portion 20. When putting on the present diaper, the side panels PL and PR are pulled around the torso of the wearer while holding the tab members 21, and the first touch fasteners F1 of the side panels PL and PR are fastened to the second touch fasteners, thereby putting the diaper on the wearer.

Note that if the outer surface side of the body portion 20 is formed by a material to which the first touch fastener F1 can be fastened, the second touch fasteners may be omitted. The body portion 20 and the panels (PR and PL) may be provided with an adhesive tape and a portion to be attached to the adhesive tape, instead of the touch fasteners.

The body portion 20 may include, for example, a pair of cuffs (anti-leak walls) to be in contact with the surface of the wearer, a liquid-permeable top sheet, the liquid-absorbing absorbent core 24, a liquid-impermeable back sheet, etc.

Note that the body portion 20 may include, for example, leg elastic threads. Moreover, the cuffs may be omitted, and elastic threads may be provided for shrinking the cuffs in the Y direction. The back sheet may be an air-permeable, waterproof sheet. The back sheet may be a stretchable sheet.

Next, an example of a production device will be described.

As shown in FIG. 3A, the present production device includes a cutter 1, an anvil roll 2, a first re-pitching drum 3, an interval-increasing drum (second re-pitching drum) 4, a phase wheel 5 and a carrier device 6.

As shown in FIG. 1, the cutter 1 successively severs, at a predetermined interval, tip portions in the flow direction Y of a continuous web W continuous in the flow direction Y, the continuous web W having been introduced onto the anvil roll 2 from a supply device 11, along a virtual severing line C extending in the width direction X perpendicular to the flow direction Y, thereby successively producing a plurality of panels PL and PR. For example, as shown in FIG. 1, the continuous web W is successively severed along severing lines C of alternating inclinations, thereby successively producing the panels PL and PR.

The virtual severing line C may be non-parallel to the width direction X, and the tip portions of the continuous web W may be successively severed by the cutter 1 along the non-parallel severing line C, thereby producing the panels PL and PR. For example, the panels PL and PR may be trapezoidal, and the panels PL and PR may be in point symmetry with each other with respect to the point O along the center line CL. The shape of the panels PR and PL may be a parallelogram, a square or a rectangle.

In FIG. 3A, the first re-pitching drum 3 includes a plurality of left and right pads 3L and 3R, wherein the interval therebetween increases and then they come closer to each other during one rotation. The first re-pitching drum 3 receives the panels PL and PR at the pads 3L and 3R, and then increases the interval P0 between the plurality of panels PL and PR of FIG. 1 in the flow direction Y to the interval P1. The left and right pads 3L and 3R (FIG. 3A) may be of a trapezoidal shape similar to the shape of the panels PL and PR.

Note that the first re-pitching drum 3 may be any of drums disclosed in US2006/0151093A1 and JP63-317576A, the content of which is herein incorporated by reference in its entirety.

An interval-increasing drum 4 of FIG. 3A is placed downstream of the first re-pitching drum 3 for increasing the interval in the width direction X between a pair of adjacent panels PL and PR of the plurality of panels PL and PR. The interval-increasing drum 4 may also implement a second re-pitching drum for increasing the pair interval P2 between one pair of panels PL and PR and another pair of panels PL and PR adjacent to the first pair of panels PL and PR, which are separated from each other in the flow direction Y.

Figure 5:
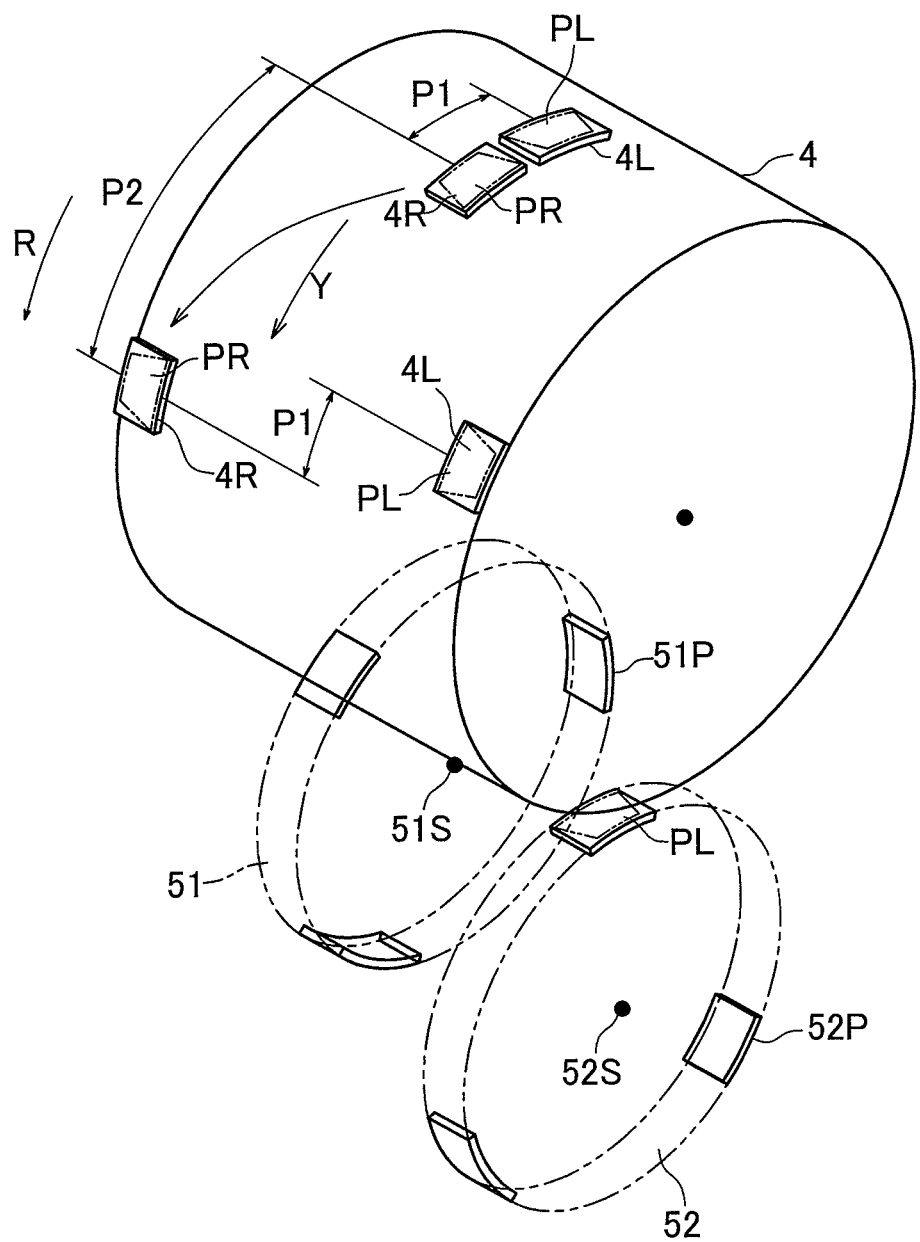
FIG. 5 is a schematic perspective view showing a second re-pitching drum and a phase wheel.

The interval-increasing drum 4 shown in FIG. 5 includes a plurality of left and right pads 4L and 4R. The interval between the pads 4L and 4R in the width direction X and the interval therebetween in the flow direction Y increase and then return to the original state while the interval-increasing drum 4 makes one rotation.

That is, while the interval-increasing drum 4 rotates in the circumferential direction R, the right pad 4R moves toward one side of the interval-increasing drum 4 and the left pad 4L moves toward the other side of the interval-increasing drum 4, thereby increasing the interval between the pad 4R and the pad 4L in the width direction X while increasing the interval in the flow direction Y between pads 4R and 4R (4L and 4L) adjacent to each other in the flow direction Y by the interval-increasing drum 4 implementing a second re-pitching drum (second re-pitching step). In the second re-pitching step, the interval between panels PL and PL (PR and PR) adjacent to each other in the flow direction is increased from (2*P1) to P2, as shown in FIG. 1.

After the panels PR and PL are handed over to first and second rollers 51 and 52, respectively, in the placement step to be described later, the width interval between the right and left pads 4R and 4L returns to the original state in order to receive the panels PR and PL again, and the interval in the flow direction between the pads, having been re-pitched, also returns to the original state.

For example, the structure of such an interval-increasing drum 4 may employ the structure of the drum disclosed in JP2006-230438A, the content of which is herein incorporated by reference in its entirety.

The phase wheel 5 of FIG. 3A includes the first and second rollers 51 and 52 placed downstream of the interval-increasing drum 4, and places each of the pair of panels PR and PL on the body portion 20.

The first axial line 51S of the first roller 51 for receiving and holding one panel PR of a pair of panels PL and PR of FIG. 5 having been separated from each other in the width direction X and the second axial line 52S of the second roller 52 for receiving and holding the other panel PL of the pair of panels PL and PR are placed offset (eccentric) by Δ from each other in the flow direction Y of the panels PL and PR.

Figure 4A:
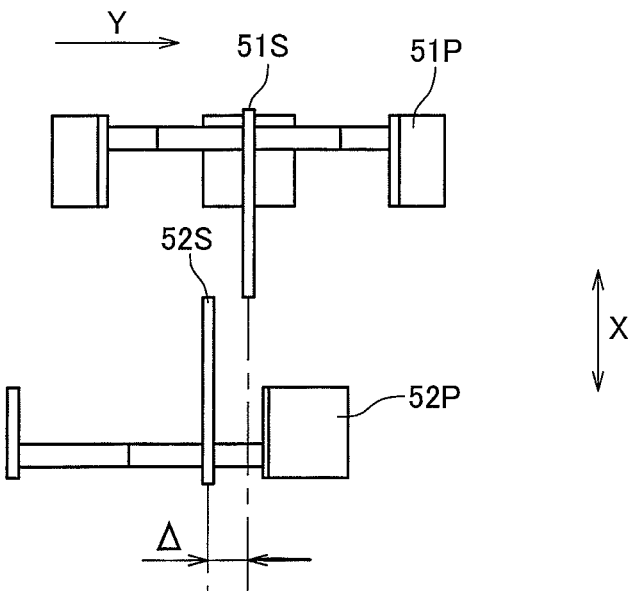
FIG. 4A is a schematic plan view showing a phase wheel.
Figure 4B:
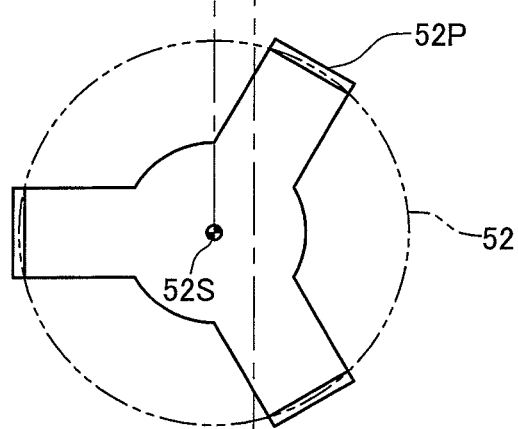
FIGS. 4B and 4C are schematic side views showing a second roller and a first roller, respectively.
Figure 4C:
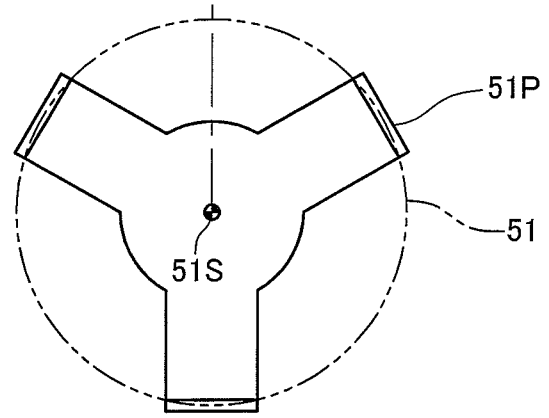

As shown in FIGS. 4A to 4C, the first and second rollers 51 and 52 respectively include a plurality of first and second pads 51P and 52P for holding the panels PL and PR. The first pad 51P and the second pad 52P are placed separated from each other in the width direction X, and the first axial line 51S, which is the center of rotation of the first pad 51P, and the second axial line 52S, which is the center of rotation of the second pad 52P, are separated from each other in the flow direction Y.

Since there is a phase difference between the right panel PR and the left panel PL, the first pad 51P and the second pad 52P for respectively receiving these panels downstream are shifted from each other in terms of the circumferential position.

Figure 7A:
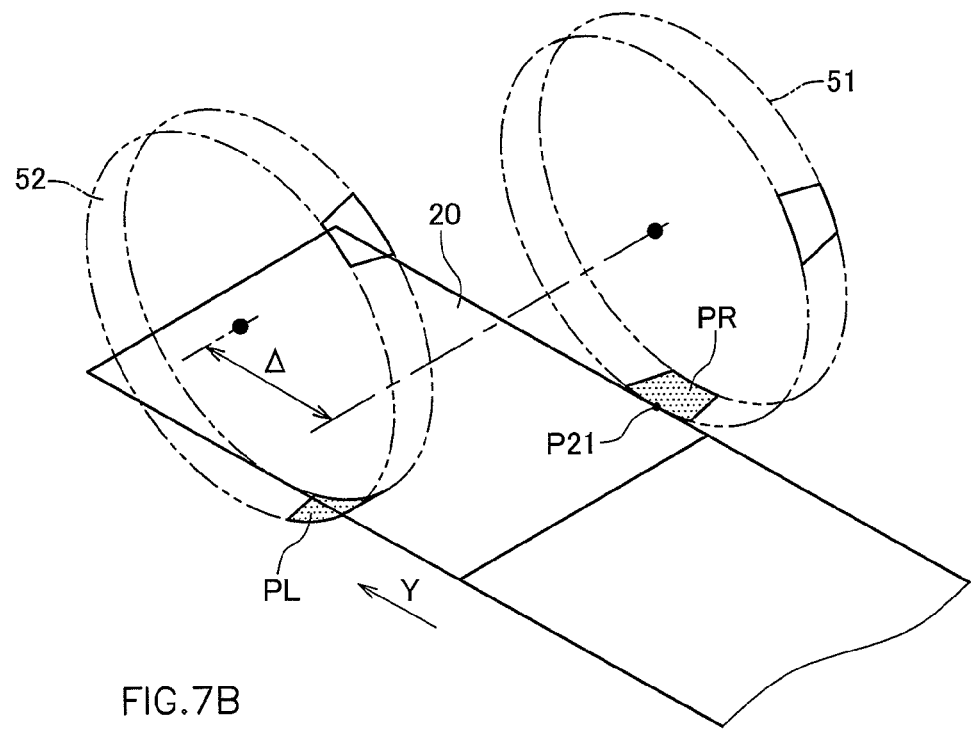
FIGS. 7A and 7B are schematic perspective views showing a placement step in which the first and second rollers place the panels on the body portion.
Figure 7B:
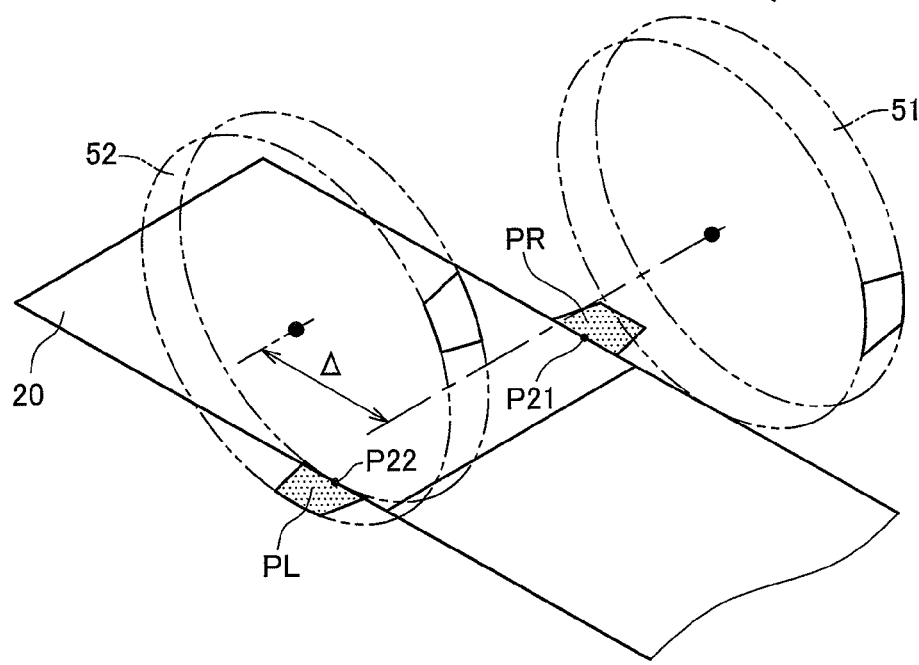
Figure 8:
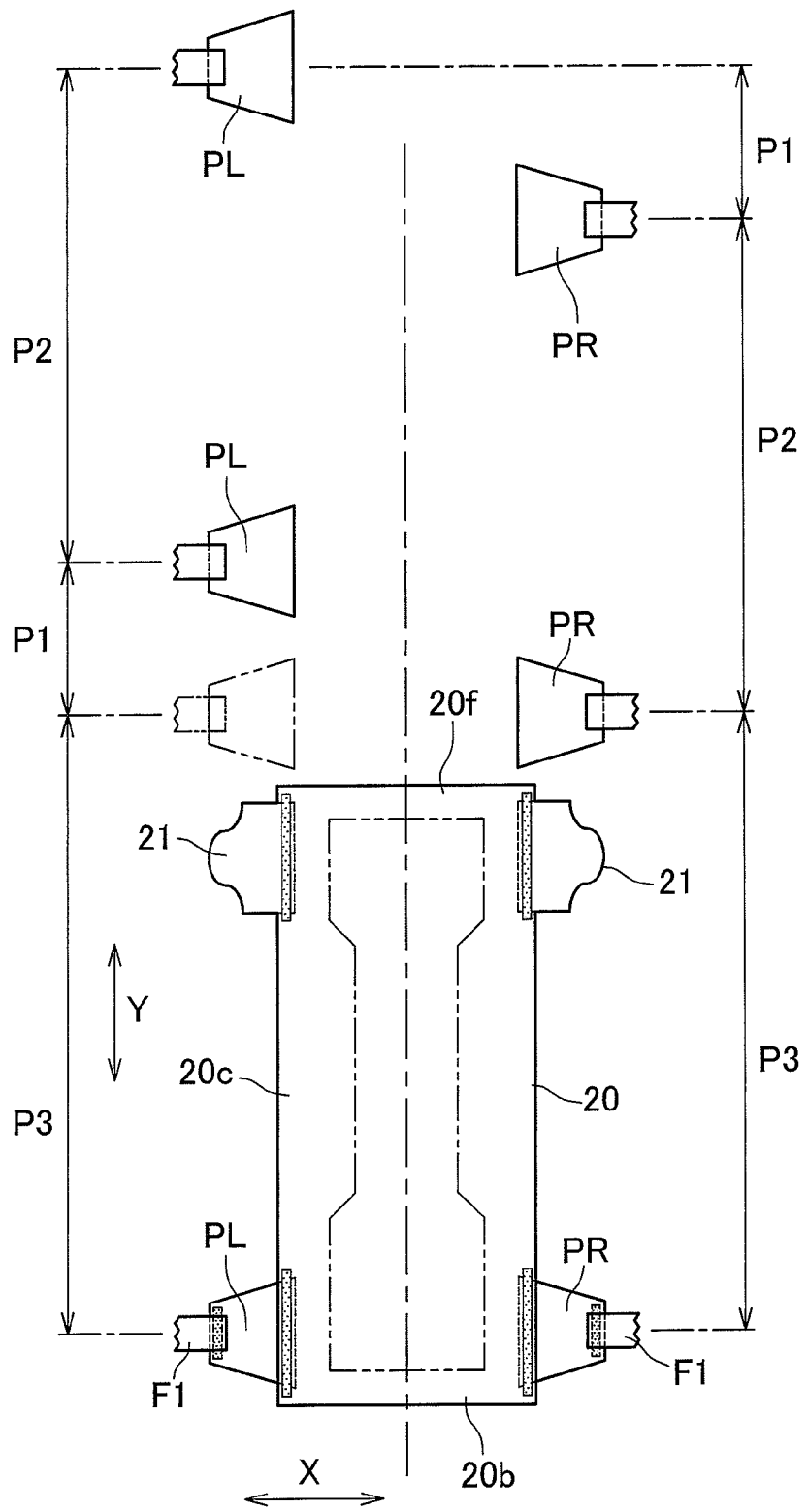
FIG. 8 is a conceptual diagram showing a part of a step of Embodiment 2.

The first and second rollers 51 and 52 receive the panels PL and PR at first and second receiving positions P11 and P12, which are separated from each other in the flow direction Y, and further place the panels PL and PR, from the first and second rollers 51 and 52 at first and second hand-over positions P21 and P22 of FIG. 3A which are separated from each other in the flow direction Y, onto opposite side portions of the body portion 20 as shown in FIGS. 7A and 7B. The pair of panels PL and PR are placed at the same position (level) of the body portion 20 in the flow direction Y. That is, they are placed so as to be positioned in left-right symmetry with respect to each other.

Note that the carrier device 6 carries the body portion 20 along a horizontal plane, for example.

Next, an example of a production method will be described.

The production method of the present embodiment includes a severing step, a first re-pitching step, an interval-increasing step, a second re-pitching step, a receiving step, and a placement step to be described below.

As shown in FIGS. 1 and 3A, in the severing step, tip portions in the flow direction Y of the continuous web W continuous in the flow direction Y are severed successively at a predetermined interval on the anvil roll 2 by the cutter 1 along the virtual severing line C extending in the width direction X, thereby successively producing a plurality of panels PL and PR. The plurality of panels PL and PR, which have been produced through the severing, are received by the pads 3L and 3R of the first re-pitching drum 3 of FIG. 3A, and then subjected to the first re-pitching step of increasing the interval in the flow direction Y of FIG. 1 from P0 of FIG. 1 to P1.

Then, after the first re-pitching step, the panels PL and PR of FIG. 1 are handed over from the first re-pitching drum 3 to the interval-increasing drum 4 of FIG. 3A. On the interval-increasing drum 4, the interval-increasing step is performed for increasing the interval in the width direction X between a pair of panels PL and PR, adjacent to each other, of the plurality of panels PL and PR of FIG. 1.

At the same time with the interval-increasing step, the second re-pitching step is performed for increasing the pair interval between a pair of panels PL and PR and another pair of panels PL and PR adjacent to the first pair of panels, separated from each other in the flow direction Y. That is, the interval between panels PR (PL) adjacent to each other in the flow direction Y is increased to P2.

In this process, there is a phase shift (phase difference) of a pitch P1 of FIG. 1 between the pair of panels PL and PR.

After the interval-increasing step and the second re-pitching step, the receiving step is performed in which the first and second rollers 51 and 52 of the phase wheel 5 receive the panels PR and PL from the interval-increasing drum 4 of FIG. 3A, and a step is further performed for placing the pair of panels PR and PL on the body portion 20.

Figure 6A:
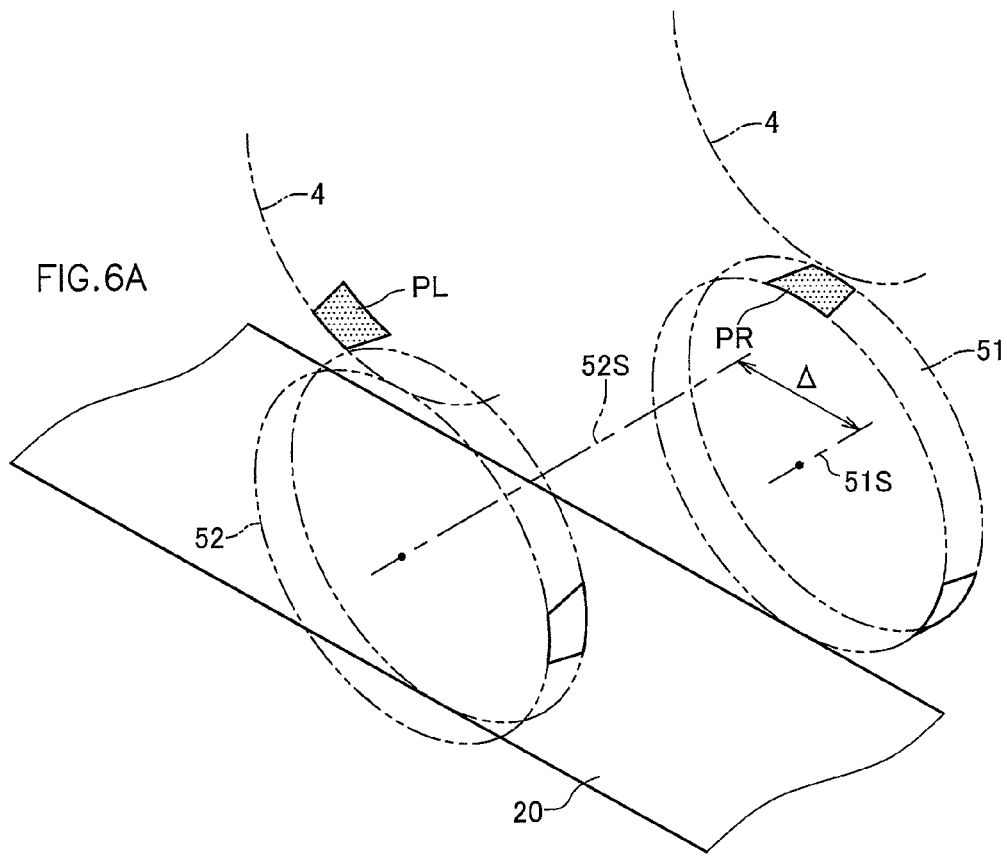
FIGS. 6A and 6B are schematic perspective views showing a receiving step in which the first and second rollers receive panels.
Figure 6B:
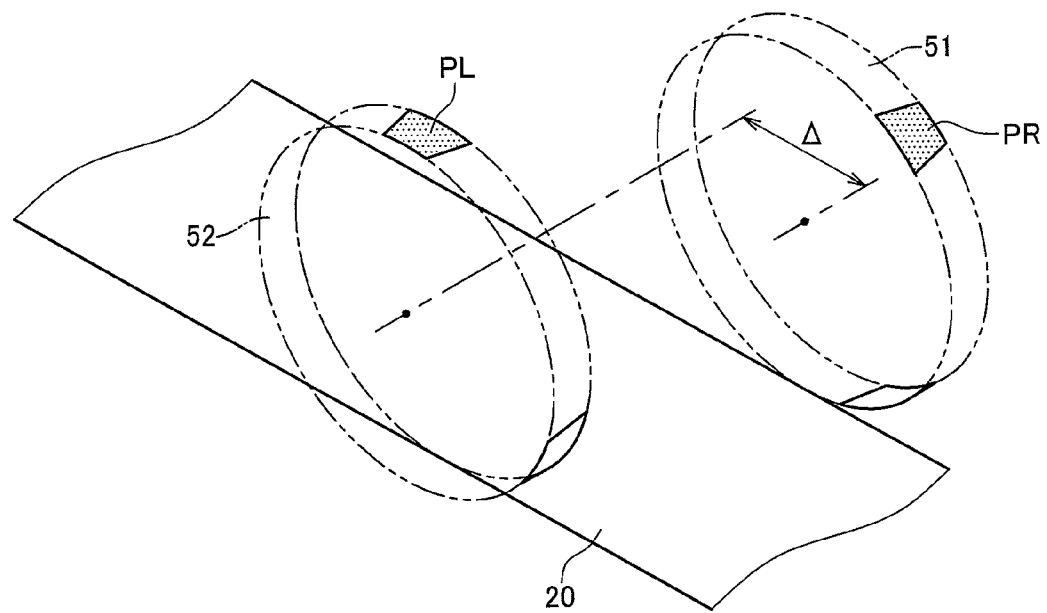

That is, first, the panel PR, which has been held by the right pad 4R of the interval-increasing drum 4 of FIG. 5, is received by the first pad 51P of the first roller 51 as indicated by the dotted area in FIG. 6A. Then, the panel PL, which has been held by the left pad 4L of the interval-increasing drum 4 of FIG. 5, is received by the second pad 52P of the second roller 52 as indicated by the dotted area in FIG. 6B. Note that while the first and second pads 51P and 52P are provided corresponding to the panels PR and PL, the pads are not drawn in FIGS. 6 and 7 for the sake of illustration.

Upon this receiving, the phase difference P1 between the pair of panels PL and PR becomes approximately (P1−Δ) since the second receiving position P12 is positioned upstream in the flow direction Y of the first receiving position P11 by an offset amount Δ. That is, the phase difference between the pair of panels PL and PR decreases.

After the receiving step, the placement step shown in FIGS. 7A and 7B is performed. That is, in this placement step, the panels PR and PL are placed from the first and second rollers 51 and 52 at the first and second hand-over positions P21 and P22 (FIG. 3A) which are separated from each other in the flow direction Y onto opposite side portions of the body portion 20.

The right panel PR is placed from the first roller 51 at the first hand-over position P21 onto one side portion of the body portion 20, as shown in FIG. 7A. Then, downstream in the flow direction Y, the left panel PL is placed from the second roller 52 at the second hand-over position P22 onto the other side portion of the body portion 20, as shown in FIG. 7B.

Now, as shown in FIG. 3A, the second hand-over position P22 is present downstream of the first hand-over position P21 by the offset amount Δ. Therefore, the phase difference between the pair of panels PL and PR changes from approximately (P1−Δ) to approximately (P1−2*Δ), and the settings are such that P1≈2*Δ, thereby making the phase difference between the pair of panels PL and PR approximately zero. That is, the pair of panels PL and PR are placed onto opposite side portions of the body portion 20 at approximately the same position in the longitudinal direction Y of the body portion 20.

Now, the principle of the present invention will be described in greater detail using FIG. 9.

Figure 9:
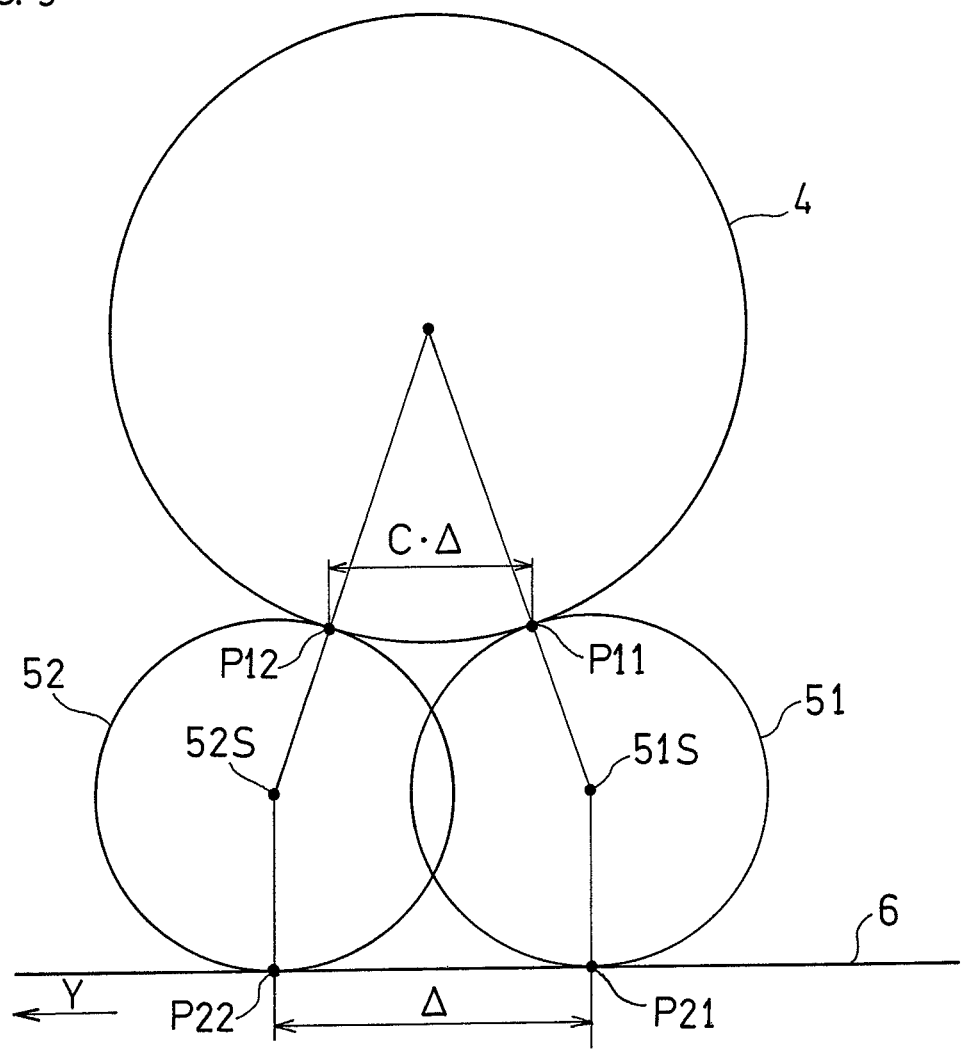
FIG. 9 is a side view showing the principle of the present invention.

As is clearly shown in FIG. 9, the offset amount C·Δ between the first receiving position P11 and the second receiving position P12 will be smaller than the offset amount Δ between the first hand-over position P21 and the second hand-over position P22. Therefore, it will not strictly be (P1=2*Δ). The difference between the offset amount C·Δ and the offset amount Δ is adjusted on site to an appropriate value.

Next, another embodiment will be described.

In the present embodiment, it is possible, with a single production device, to produce different sizes of body portions 20 without switching parts from one to another.

The length of the body portion 20 is different for each size of the body portion 20. Therefore, the interval (pitch) P2 between adjacent pairs of panels PL and PR needs to be changed to P3. For such an interval change, a variable-speed control device (not shown) is provided in the present embodiment.

The variable-speed control device controls a servo motor, for example, so as to periodically vary the rotation speed of a plurality of pads 51P and 52P of the rollers 51 and 52 holding the panels PL and PR, from the receiving until the placement, a number of times equal to the number of pads 51P, 52P for one rotation according to the size of the worn article. For example, where the size of the body portion 20 is longer than standard, the phase wheel 5, placed downstream of the interval-increasing drum 4, successively receives a plurality of pairs of panels PL and PR with an increased pair interval therebetween, and further increases the pair interval from P2 to P3 after the receiving.

The method for such a periodic speed variation, where a main motor and an auxiliary servo motor are used, is disclosed, for example, in JP2002-35027A, the content of which is herein incorporated by reference in its entirety.

Next, a production method of the present embodiment will be described. The present embodiment includes a third re-pitching step, wherein the pair interval is further increased from P2 to P3 after the receiving step of successively receiving a plurality of pairs of panels PL and PR onto the phase wheel 5 from the interval-increasing drum 4, the pair interval therebetween having been increased after the second re-pitching step. That is, the method further includes a speed varying step of periodically varying the rotation speed of a plurality of pads 51P and 52P of the first and second rollers 51 and 52 holding the panels PL and PR between the receiving step and the placement step a number of times equal to the number of pads 51P, 52P (three times in the case of FIG. 4) for one rotation according to the size of the worn article.

Incidentally, with the production device of FIG. 3A, the radii of rotation of the first pad 51 and the second pad 52 may be equal to each other, but the radii of rotation may be different from each other. In this case, the carrying plane of the carrier device 6 will be inclined with respect to horizontal.

The rollers and the drums 1 to 5 of FIG. 3A may be arranged horizontally instead of vertically in order to reduce the load accumulating on the shafts, in which case the carrying plane of the carrier device 6 may be set to be vertical.

While preferred embodiments have been described above with reference to the drawings, obvious variations and modifications will readily occur to those skilled in the art upon reading the present specification.

For example, there may be no phase wheel 5.

The worn article may be diaper-shaped or pants-shaped.

Thus, such changes and modifications are deemed to fall within the scope of the present invention, which is defined by the appended claims.

INDUSTRIAL APPLICABILITY

The present invention is applicable to a method for producing a disposable worn article, and a device for producing the same.

REFERENCE SIGNS LIST

1: Cutter, 11: Supply device
2: Anvil roll
20: Absorbent body portion, 20b: Rear torso portion, 20c: Crotch portion, 20f Front torso portion
21: Tab member
3: First re-pitching drum, 3L,3R: Left and right pads
4: Interval-increasing drum (second re-pitching drum), 4L,4R: Left and right pads
5: Phase wheel, 51,52: First and second rollers, 51S: First axial line
52S: Second axial line, 51P,52P: First and second pads
6: Carrier device
C: Severing line, CL: Center line
F1: First touch fastener
O: Point
PL,PR: Side panel
P1,P1: Interval, P2: Pair interval, P11,P12: First and second receiving positions
P21,P22: First and second hand-over positions
X: Width direction, y: Flow direction
W: Continuous web

The invention claimed is:

1. A method for producing a disposable worn article, in which a pair of panels are fastened to a body portion at the same position in a longitudinal direction thereof and in left and right opposite side portions in a girth direction thereof, the method comprising:
a severing step of successively severing tip portions of a continuous web in a flow direction, the continuous web being continuous in the flow direction, along a virtual severing line extending in a width direction perpendicular to the flow direction, thereby successively producing a plurality of panels;
an interval-increasing step of increasing an interval in the width direction between a pair of panels, adjacent to each other in the flow direction, of the plurality of panels;
a receiving step of receiving the panels by first and second rollers at first and second receiving positions, which are separated from each other in the flow direction, wherein the first and second rollers are placed so that a first axial line of the first roller for receiving and holding one of the pair of panels separated from each other in the width direction and a second axial line of the second roller for receiving and holding the other one of the pair of panel's are placed offset from each other in the flow direction of the panels; and
a placement step of placing the panels, from the first and second rollers at first and second hand-over positions which are separated from each other in the flow direction, onto the opposite side portions of the body portion at the same position in the longitudinal direction of the body portion.

2. A method according to claim 1, further comprising a re-pitching step of increasing an interval in the flow direction between a pair of panels, adjacent to each other in the flow direction, of the plurality of panels.

3. A method according to claim 1, further comprising a speed varying step of periodically varying a rotation speed of a plurality of pads of the rollers holding the panels between the receiving step and the placement step a number of times equal to the number of pads for one rotation according to a size of the worn article.

4. A device for producing a disposable worn article, in which a pair of panels are fastened to a body portion at the same position in a longitudinal direction thereof and in left and right opposite side portions in a girth direction thereof, the device comprising:
a cutter for successively severing tip portions of a continuous web in a flow direction, the continuous web being continuous in the flow direction, along a virtual severing line extending in a width direction perpendicular to the flow direction, thereby successively producing a plurality of panels;
an interval-increasing drum for increasing an interval in the width direction between a pair of panels, adjacent to each other in the flow direction, of the plurality of panels; and
a phase wheel for receiving the panels by first and second rollers at first and second receiving positions, which are separated from each other in the flow direction, wherein the first and second rollers are placed so that a first axial line of the first roller for receiving and holding one of the pair of panels separated from each other in the width direction and a second axial line of the second roller for receiving and holding the other one of the pair of panels are placed offset from each other in the flow direction of the panels, and for placing the panels, from the first and second rollers at first and second hand-over positions which are separated from each other in the flow direction, onto the opposite side portions of the body portion at the same position in the longitudinal direction of the body portion.

5. A production device according to claim 4, wherein:
the first roller includes a plurality of first pads rotating about the first axial line while holding the panels;
the second roller includes a plurality of second pads rotating about the second axial line while holding the panels;
the plurality of first pads and the plurality of second pads are placed separated from each other in the width direction; and
the first axial line and the second axial line are separated from each other in the flow direction.

6. A production device according to claim 5, wherein radii of rotation of the first pads and the second pads are equal to each other.

7. A device according to claim 6, further comprising a re-pitching drum placed between the cutter and the interval-increasing drum for increasing an interval in the flow direction between a pair of panels, adjacent to each other in the flow direction, of the plurality of panels.

8. A production device according to claim 6, further comprising a variable-speed control device for periodically varying a rotation speed of a plurality of pads of the rollers holding the panels, from the receiving until the placement, a number of times equal to the number of pads for one rotation according to a size of the worn article.

9. A method for producing a disposable worn article, in which a pair of panels are fastened to a body portion in left and right opposite side portions in a girth direction thereof, the method comprising:
a severing step of successively severing tip portions of a continuous web in a flow direction, the continuous web being continuous in the flow direction, along a virtual severing line extending in a width direction perpendicular to the flow direction, thereby successively producing a plurality of panels;

a first re-pitching step of increasing an interval in the flow direction between the plurality of panels;

an interval-increasing step of, after the first re-pitching step, increasing an interval in the width direction between a pair of panels, adjacent to each other, of the plurality of panels; and a placement step of, after the interval-increasing step, placing the pair of panels in the opposite side portions of the body portion.

10. A method according to claim 9, wherein the virtual severing line is non-parallel to the width direction, and the tip portions of the continuous web are successively severed in the severing step along the non-parallel severing line, thereby producing the panels.

11. A method according to claim 10, further comprising a second re-pitching step of increasing a pair interval between a pair of panels, which have been separated from each other in the flow direction in the first re-pitching step, and another pair of panels adjacent to the pair of panels.

12. A method according to claim 11, further comprising:

a receiving step of successively receiving a plurality of pairs of panels, the pair interval therebetween having been increased after the second re-pitching step, from an upstream device to a downstream device; and a third re-pitching step for further increasing the pair interval after the receiving step.

13. A device for producing a disposable worn article, in which a pair of panels are fastened to a body portion in left and right opposite side portions in a girth direction thereof, the device comprising:

a cutter for successively severing tip portions of a continuous web in a flow direction, the continuous web being continuous in the flow direction, along a virtual severing line extending in a width direction perpendicular to the flow direction, thereby successively producing a plurality of panels;

a first re-pitching drum for increasing an interval in the flow direction between the plurality of panels;

an interval-increasing drum, placed downstream of the first re-pitching drum, for increasing an interval in the width direction between a pair of panels, adjacent to each other, of the plurality of panels; and a phase wheel, placed downstream of the interval-increasing drum, for placing the pair of panels in the opposite side portions of the body portion.

14. A production device according to claim 13, wherein the virtual severing line is non-parallel to the width direction, and the tip portions of the continuous web are successively severed by the cutter along the non-parallel severing line, thereby producing the panels.

15. A production device according to claim 14, further comprising a second re-pitching drum, placed downstream of the first re-pitching drum, for increasing a pair interval between a pair of panels, which have been separated from each other in the flow direction, and another pair of panels adjacent to the pair of panels.

16. A production device according to claim 15, wherein the phase wheel, placed downstream of the second re-pitching drum, successively receives a plurality of pairs of panels, the pair interval therebetween having been increased, and further increases the pair interval after the receiving.

* * * * *